United States Patent [19]

Kluksdahl et al.

[11] Patent Number: 5,266,727
[45] Date of Patent: Nov. 30, 1993

[54] PURIFICATION OF ALKYL SULFIDES

[75] Inventors: Harris E. Kluksdahl, San Rafael; Gary M. H. Lee, Hercules, both of Calif.

[73] Assignee: Chevron Research and Technology Company, San Francisco, Calif.

[21] Appl. No.: 911,848

[22] Filed: Jul. 10, 1992

[51] Int. Cl.$^5$ ............................................. C07C 319/28
[52] U.S. Cl. .......................................... 568/60; 568/59
[58] Field of Search ..................................... 568/59, 60

[56] References Cited

U.S. PATENT DOCUMENTS 3,985,552  10/1976  Edwards ............................. 75/101

Primary Examiner—Marianne M. Cintins
Assistant Examiner—Margaret Page
Attorney, Agent, or Firm—W. K. Turner; R. J. Sheridan

[57] ABSTRACT

A process for purifying alkyl sulfides by absorption of the organosulfur impurities on an absorbent. The absorber is a copper salt deposited on a high surface area support. The purified alkyl sulfide is useful as an extractant for palladium.

7 Claims, No Drawings

PURIFICATION OF ALKYL SULFIDES

BACKGROUND OF THE INVENTION

The present invention lies in the art of refining platinum group metals (PGM's) through solvent extraction. More specifically, the invention relates to a process for purifying alkyl sulfide extractant for use in extracting palladium from a mixture of palladium and other PGM's. In particular, the process is directed to the removal of organosulfur compounds from alkyl sulfide extractant, as they interfere with the recovery of palladium.

Solvent extraction of aqueous solutions containing precious metals derived from ores and their subsequent products is gaining in use due to its advantages over the classical precipitation and redissolution methods. Advantages of solvent extraction include a reduced cycle time, higher purity, and often higher yields. With proper selection of solvents and process conditions, extraction can be highly specific for a particular metal species, resulting in recovery of a high purity product. Typically, the required purity of PGM's is up to about 99.995%. To achieve this level of purification using precipitation and redissolution procedures requires multiple repeat processing and thus considerable time. Solvent extraction shortens the time for purification many fold, while yielding a higher purity product.

Solvent extraction is carried out by contacting an aqueous phase solution of one or more extractable metals with an organic phase containing the extractant. The extractable metal or metals form complex compounds, with the extractant acting as the complexing agent or ligand. Each of the extractable metals can form one or more complexes with different atomic or molecular entities occupying ligand positions in the coordination spheres of the complexes. These ligands can be anions (chloride and other halides, sulfate, nitrite), cations (nitrosyl, $NO^+$), neutral species ($H_2O$, $NH_3$) or organic compounds (ethers and other oxygenated compounds, amines, sulfides). For those metals exhibiting more than one valence state, some of which can be easily reduced (e.g. Au(III), Pd(IV) and Ir(IV)), care must be taken in achieving the desired chemistry for extraction and stripping. Large differences in rates of reduction and ligand substitution reactions result in separation between metal species. Sequential extractions using different extractant enables separation of a plurality of metal species from a single solution.

For recovery of palladium (Pd) from ores containing Pd and other PGM's, various alkyl sulfides have been used as extractant. For such an example, see U.S. Pat. No. 3,985,552 issued Oct. 12, 1972 to Edwards. In a typical extraction, a diluent such as a paraffinic or aromatic liquid is combined With the alkyl sulfide to form an organic phase. An aqueous phase, usually an aqueous acidic chloride solution containing Pd and other metals extracted from the ore, is contacted with the organic phase. The Pd in the aqueous phase forms a complex with the extractant and, due to its high solubility in the organic phase, the Pd complex is almost completely partitioned into the organic phase. Using n-octylsulfide (NOS) as the extractant, for example, the equation for extraction is:

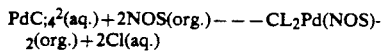

$$PdC_4^2(aq.) + 2NOS(org.) \text{---} CL_2Pd(NOS)_2(org.) + 2Cl(aq.)$$

In typical commercial practice, the organic phase is first washed with a dilute HCL solution to remove entrained raffinate comprising other PGM's and small amounts of other metals, such as iron and copper, which are extracted to a low level. The washed, loaded organic phase, containing less contaminant metals, is then stripped using aqueous ammonia The Pd complexes with the ammonia to form $Pd(NH_3)_4^{2+}$ ion in aqueous solution. The extractant is then recycled for reuse. The aqueous Pd solution, which also contains excess $NH_3$ and Cl, is then carefully acidified to precipitate the sparingly soluble salt $Cl_2Pd(NH_3)_2$. Conversion to the metal results by its ignition at high temperature (e.q., about 900° C.) to form "Pd sponge."

The extraction and stripping of PGM's using alkyl sulfides is affected by organosulfur impurities such as mercaptans and disulfides present in the alkyl sulfides. During stripping the organosulfur impurities readily react with palladium and other PGM's to form a solid emulsion-like "crud" phase which disrupts the complete recovery of Pd. For example, sulfur compounds, such as mercaptans, are undesirable in the alkyl sulfide as they can tie up metals as the mercaptides and can subsequently cause problems in the stripping step. These problems can be overcome by using highly purified alkyl sulfides, but at considerable added materials cost.

There is a need for a process for conveniently and efficiently purifying the alkyl sulfides which are used for purifying palladium and other PGM's, of the unwanted impurities. This need is met by the present invention.

SUMMARY OF THE INVENTION

It is accordingly an object of the invention to provide alkyl sulfides having a purity sufficient to extract palladium from a solution of palladium and other platinum group metals, without the formation of significant side reactions and/or by-products, in a metals recovery process, and to give a high recovery of palladium as well.

It is another object of the invention to provide a process, as above, whereby a sufficiently pure alkyl sulfide is obtained at an economical cost.

It is a further object of the invention to provide a process for removing organosulfur impurities from alkyl sulfides.

These above objectives, and others, are achieved by a process for purifying an alkyl sulfide containing organosulfur impurities, which comprises the steps of contacting the alkyl sulfide with an absorbent comprising at least one metal or compound thereof, selected from the Group IB and Group IIB metals, deposited on a porous, high area support, absorbing the organosulfur impurities on the absorber thereby purifying the alkyl sulfide, and recovering the purified alkyl sulfide.

As used herein, Group IB metals include copper, silver, and gold, and Group IIB metals include zinc, cadmium, and mercury. The preferred Group IB metal is copper. The preferred Group IIB metal is cadmium. Copper is particularly preferred.

The objectives of the invention are also achieved by a process for extracting palladium from an aqueous solution, which comprises the steps of contacting the aqueous solution with an organic solvent containing a purified alkyl sulfide, extracting the palladium from the aqueous solution into the organic solvent, and stripping the palladium from the organic solvent. The purified alkyl sulfide is obtained by removing organosulfur impurities from an alkyl sulfide. The purification includes the steps of contacting the alkyl sulfide with an absorber comprising at least one metal, or compound thereof, selected from the Group IB and Group IIB metals, deposited on a porous, high area support, and absorbing the organosulfur impurities in the absorber. The alkyl sulfide is thereby purified and is thereafter recovered.

DETAILED DESCRIPTION OF THE PREFERRED EMBODIMENTS

The alkyl sulfides used in the present process have the generic chemical formula R-S-R, where R is a straight- or branched-chain alkyl group. Paraffins having six to nine carbon atoms are preferred. N-octyl sulfide (NOS) is an example of an alkyl sulfide which is useful in the present process.

Alkyl sulfides, as prepared by commercial processes, commonly contain small concentrations of organosulfur impurities, including mercaptans, where mercaptans have the generic chemical formula R-S-H. Unexpectedly, using alkyl sulfides containing organosulfur impurities for extracting palladium compounds from aqueous solution has been found to provide unsatisfactory yields of Pd due to the formation of a solid "crud" during the stripping step which is inseparable from both aqueous and organic phases. While not limiting the present invention in any way or any theory of operation, the emulsions formed by the "crud" are thought to be caused by reaction of the organosulfur impurities with palladium compounds. Organosulfur concentrations as low as 200 ppm or less can disrupt the palladium stripping, and they further complicate the separation of alkyl sulfide from the "crud."

Alkyl sulfides are purified, according to the invention, using an absorber which comprises a metal salt deposited on a high area support. By the term "high area support" we mean a porous support which is selected to maximize the amount of absorber metal which is available for absorption and/or reaction with the organosulfur impurities. One objective in selecting an appropriate support is the degree of interaction between the metal and the support. Excessive interaction may inhibit the absorption process. Insufficient interaction may render the metal easily removed from the support. Thus, supports such as high surface area silicas and aluminas are preferred, and alumina is particularly preferred.

The process by which the alkyl sulfide is contacted with the absorber is not critical to the invention, so long as the organosulfur content of the alkyl sulfide is reduced. Thus, the alkyl sulfide may be passed over a bed of absorber in any absorption column. Alternatively, a layer of absorber may be placed in a container of stirred alkyl sulfide.

More thorough purification steps, such as distillation, which removes other impurities besides organosulfur compounds, provide a benefit in removing trace levels of the undesirable impurities.

The absorber used in the present process comprises at least one metal or compound thereof selected from the Group IB and Group IIB metals, deposited on a porus, high area support. Group IB metals include copper, silver, and gold, and Group IIB metals include zinc, cadmium, and mercury. The preferred Group IB metal is copper. The preferred Group IIB metal is cadmium. Copper is particularly preferred. The metal is deposited on the support using methods known to the art. A preferred deposition method is by aqueous impregnation of the metal salt, followed by drying of the impregnated support at elevated temperatures of from about 70° to about 200° C., preferably at about 125° C. for a period sufficient to completely or substantially remove the aqueous solvent. The solution of metal salt used for aqueous impregnation is from about 1M to saturation concentration at ambient temperature with about 3M to saturation preferred. Alternatively, the metal can be chemisorbed by ion exchange onto the support from a solution of the soluble metal salt. Typical metal salts used for preparing the absorbent include sulfates, nitrates, acetates, and halides, including fluoride, chloride, bromide and iodide.

The support is mixed with the metal salt solution in a weight ratio of metal salt to support of from about 5:1 to about 1:5, preferably from about 3:1 to about 1:3 and most preferably about 1:1.

The purification process of the invention is capable of reducing the mercaptan level to less than about 5 ppm from an initial concentration of greater than 200 ppm. In many instances the level of mercaptan is reduced to below about 2 ppm and can sometimes be reduced to below about 1 ppm.

The following examples are intended only to illustrate the invention, and not limit the claimed invention in any way.

COMPARATIVE EXAMPLE

Commercially available n-octyl sulfide manufactured by Phillips Petroleum was used as received to extract Pd. The NOS contained approximately 243 ppm mercaptan sulfur as well as other sulfur compounds and impurities which could not be readily identified. The NOS was dispersed in a kerosene solvent at a 50:50 Weight ratio and mixed with an aqueous solution of pd and other pGM's. Extraction of pd was carried out successfully. However, attempts to strip the Pd from the NOS produced unacceptable emulsions and phase separation problems.

EXAMPLE 1

Metal salts of Cu and Cd were deposited on high surface area supports in preparation for use in purifying NOS.

Each metal salt was dissolved in distilled water, and the support was impregnated by the pore fill procedure. Each absorbent was dried at approximately 258° F. and then used directly or, in some cases, dried in air at higher temperatures (600°-800° F.). Table I summarizes the materials prepared.

TABLE I

| Absorber | Elemental Metal Content, Wt % | Support |
|---|---|---|
| $CuCl_2/SiO_2$ | 9.7 | High Area Silica Davison Grade 408 |
| $Cu(COOCH_3)_2/SiO_2$ | 3.3 | High Area Silica Davison Grade 408 |
| $CuSO_4/Al_2O_3$ | 5.8 | Activated Alumina Extrudate |
| $Cd(NO_3)_2/SiO_2$ | 16.2 | Davison Grade 408 |
| $CdSO_4/SiO_2$ | 12.4 | Davison Grade 408 |
| $CdSO_4/Al_2O_3$ | 9.1 | Activated Alumina Extrudate |
| Absorbent A* | — | — |
| Absorbent B* | — | — |

*Sulfur sorbent materials used in the petroleum refining industry.

EXAMPLE 2

Different absorbent systems were evaluated With NOS and also with a special solution comprising 250 ppm sulfur as n-octyl mercaptan (NOM) in Isopar L, a pure, highly isomerized kerosene fraction manufactured by Exxon, and which was further purified with activated silica gel. The level of 250 ppm mercaptan sulfur approximates the level present in commercially available NOS.

Testing of an absorbent involved contacting it for several days (with periodic shaking) in a closed container with each organic solution (1:3 weight ratio of absorber to solution). In some cases, a second contacting stage with activated alumina was used to remove color from the solution. This color was attributed to dissolved metal salts from the absorber. Filtering was also employed whenever particulates were observed.

Table II summarizes the results in the test of adsorbents with the special test solution containing 250 ppm mercaptan sulfur. The key measurements of interest are residual mercaptan sulfur level, the non-alkyl sulfide sulfur level, and the amount of metal transferred into the organic phase.

mercaptan sulfur: 3 ppm for copper acetate [Cu(OOCCH$_3$)$_2$]and 67 ppm for CdSO$_4$. The non-alkyl sulfide sulfur values (100 ppm and 55 ppm, respectively), however, suggested that mercaptan sulfur had been changed to another sulfur compound.

A second treatment of the solution with activated alumina lowered the mercaptan sulfur to acceptable levels but not the non-alkyl sulfide sulfur values. This shows that metal salts on silica gel supports did not completely remove sulfur compounds. It further suggests that the mercaptans are converted to non-polar sulfur compounds, very likely disulfides, which apparently are not readily absorbed by oxide adsorbents.

As also summarized in Table II, two commercial adsorbents used in the petroleum industry, identified as "A" and "B", gave acceptable purification of the special test solution. Both lowered the mercaptan sulfur to less than 2 ppm and the non-alkyl sulfide sulfur to less than 5.5 ppm.

EXAMPLE 3

Various compositions were evaluated for removal of non-alkyl sulfide sulfur from NOS. CuSO$_4$ dispersed on activated alumina extrudate (alone or followed by a

TABLE II

REMOVAL OF MERCAPTAN AND OTHER IMPURITIES FROM AN n-OCTYL MERCAPTAN REFERENCE SOLUTION USING VARIOUS ABSORBERS

| Item | Absorber - Purification Process | Metal Content Wt % | Thermal Condition of Absorber, °F. | Metal from Absorber Conc., ug/g | Mercaptan Conc., ppm | Total[6] Sulfur Conc., ppm |
|---|---|---|---|---|---|---|
| 1 | Mercaptan Reference Solution; No Treatment | — | None | | 256 251; 251 | 295 |
| 2 | Mercaptan Reference Solution; No Treatment | — | None | | 246 249 | 290 |
| 3 | Activated Al$_2$O$_3$ Extrudated | — | 600[2] | | <5 | 146 |
| | *Copper Containing Absorbers* | | | | | |
| 4 | 1. Cu(COOCH$_3$)$_2$/SiO$_2$ | 3.3 | 130[1] | | <3 | 100 |
| 5 | 2. First: Cu(COOCH$_3$)$_2$/SiO$_2$ Second: Activated Al$_2$O$_3$ | 3.3 | 130[1] Alumina[2] at 600 | Cu <0.8 | <3 | 24.3; 23.5 |
| 6 | 3. CuSo$_4$/Al$_2$O$_3$ | 5.8 | 830[2] | Cu <0.4 | <2 | 6.9 |
| 7 | 4. First: CuSO$_4$/Al$_2$O$_3$ Second: Activated Al$_2$O$_3$ | 5.8 | 830[2] Alumina[2] at 600 | Cu <0.4 | <2 | 2.8 |
| 8 | 5. First: CuSO$_4$/Al$_2$O$_3$ Second: Activated Al$_2$O$_3$ | 5.8 | 830[2] Alumina[2] at 800 | Cu <0.4 | 1 | 4.6 |
| | *Cadmium-Containing Absorbers* | | | | | |
| 9 | 1. CdSO$_4$/SiO$_2$ | 12.4 | 258[1] | Cd <0.03 | 67 | 55 |
| 10 | 2. First: CdSO$_4$/SiO$_2$ Second: Activated Al$_2$O$_3$ | 12.4 | 258[1] Alumina[2] at 600 | Cd <0.03 | <3 | 35.6 |
| 11 | 3. CdSO$_4$/Al$_2$O$_3$ | 9.1 | 291[1] | Cd <0.03 | <3 | 2.59 |
| | *Commercial Absorbents* | | | | | |
| 12 | 1. Absorbent A[4] | — | 750[3] | <0.5 <0.5 | <2 | 4.49 4.21 |
| 13 | 2. Absorbent B[4] | — | 750[3] | <0.5 <0.5 | <2 | 3.44 2.44 |

[1]Dried under vacuum with a N$_2$ purge.
[2]Previously calcined in muffle furance.
[3]Freshly calcined; sample used immediately.
[4]Sulfur sorbent material used in the petroleum industry.
[5]Excludes Alkyl Sulfide Sulfur.

The best absorbent systems were CuSCO$_4$ or cadmium sulfate (CdSO$_4$) salts supported on activated alumina extrudate. Both were extremely effective in removing mercaptans and non-alkyl sulfide sulfur compounds from the test solution. An additional treatment with activated alumina did not improve sulfur removal any further for the CuSCO$_4$ absorbent system as seen from Table II, Items 7 and 8.

As shown in Table II, metal salts dispersed on activated silica gel were partially effective in lowering second contacting with activated alumina) produced the most acceptable purified NOS, containing less than 0.5 ppm copper (Cu) and less than 2 ppm mercaptan sulfur. (This is shown in Table III.) More importantly, the purified NOS performed well in the solvent extraction of Pd (no separation or emulsion problems arose in either extraction or stripping).

Table III summarizes the mercaptan removal and metals transfer with the adsorbents listed in Table I.

TABLE III

REMOVAL OF MERCAPTAN AND OTHER IMPURITIES FROM HEAT n-OCTYL SULFIDE USING VARIOUS ABSORBERS

| Item | Absorber - Purification Process | Metal Content Wt % | Thermal Pretreatment of Absorber, °F. | Metal from Absorber Conc., ug/g | Mercaptan Conc., ppm |
|---|---|---|---|---|---|
| 1 | NOS, No Treatment | — | — | | 245;241 |
| 2 | Activated $SiO_2$ (Davison Grade 923) | — | $600^2$ | | 211;207 |
| 3 | Activated $Al_2O_3$ Extrudate | — | — | | 86 |
|   | *Copper Containing Absorbers* | | | | |
| 4 | 1. $CuCl_2/SiO_2$ | 9.7 | $200^1$ | 12,100 | Not Submitted[5] |
| 5 | 2. $CuCl_2/SiO_2$, Three Dilute HCl Washes (1 M and 0.1 M HCl) | 9.7 | $200^1$ | 720;728 | Not Submitted[5] |
| 6 | 3. $CuCL_2/SiO_2$ (0.1 M HCl Wash) | 9.7 | $200^1$ | 2,710 | Unable to Analyze[4] |
| 7 | 4. $Cu(COOCH_3)_2/SiO_2$ | 3.3 | 125 | 369 | Not Submitted[6] |
| 8 | 5. First: $Cu(COOCH_3)_2/SiO_2$ | 3.3 | $125^1$ | | |
|   | Second: Activated $Al_2O_3$ | | Alumina at $600^2$ | 50.2; 45.6 | <2 |
| 9 | 6. First: $Cu(COOCH_3)_2/SiO_2$ | 3.3 | $125^1$ | | |
|   | Second: Activated $Al_2O_3$ | | Alumina at $600^2$ | <1, <1 | Not Submitted[6] |
| 10 | 7. $Cu(COOCH_3)_2/SiO_2$ | 3.3 | $90^1$ | 353 | Not Submitted[5] |
| 11 | 8. First: $Cu(COOCH_3)_2/SiO_2$ | | $90^1$ | | |
|   | Second: Activated $Al_2O_3$ | | Alumina at $600^2$ | <0.1 | <2 |
| 12 | 9. $CuSO_4/Al_2O_3$ | 5.8 | $830^2$ | 0.5 | <2 |
| 13 | 10. First: $CuSO_4/Al_2O_3$ | 5.8 | $830^2$ | | |
|   | Second: Activated $Al_2O_3$ | | Alumina at $600^2$ | <0.4 | <1 |
| 14 | 11. First: $CuSO_4Al_2O_3$ | 5.8 | $830^2$ | | |
|   | Second: Activated $Al_2O_3$ | | Alumina at $800^2$ | <0.4 | <2 |
|   | *Cadmium Containing Absorbents* | | | | |
| 15 | 1. $Cd(NO_3)_2/SiO_2$ | 16.2 | $257^1$ | 11 | Not Submitted[5] |
| 16 | 2. First: $Cd(NO_3)_2/SiO_2$ | 16.2 | $257^1$ | | |
|   | Second: Activated $Al_2O_3$ | | Alumina at $600^2$ | <2 | <5 |
| *17 | 3. $CdSO_4/SiO_2$ | 12.4 | $259^1$ | <5 | Not Submitted[5] |
| 18 | 4. First: $CdSO_4SiO_2$ | 12.4 | $259^1$ | | |
|   | Second: Activated $Al_2O_3$ | | Alumina at $600^2$ | <1 | <1 |
| 19 | 5. $CdSO_4/Al_2O_3$ | 9.1 | $219^1$ | <0.1 | <8 |
|   |   |   |   |   | 14, 16, 16[7] |
| 20 | 6. First: $CdSO_4/Al_2O_3$ | 9.1 | $219^1$ | | |
|   | Second: $SiO_2$ | | | | 18 |
| 21 | 7. $CdSO_4/Al_2O_3$ | 9.1 | $219^1$ | <0.03 | 4 |
| 22 | 8. $CdSO_4/Al_2O_3$ | 9.1 | $900^3$ | <0.21 | 3 |

[1] Dried under vacuum with a $N_2$ purge.
[2] Previously calcined in muffle furance.
[3] Freshly calcined; sample used immediately.
[4] The solution was not titrated to end point. The indicator turned blue immediately upon contact with the solution.
[5] The solution was colored, indicated the presence of a metal ion which could have interfered with the mercaptan determination.
[6] Insufficient sample for analysis.
[7] One month later, the sample had an odor of $H_2S$ (analyzed 3-5 ppm) and higher mercaptan sulfur values.

$CdSO_4$ on activatd alumina extrudate produced an NOS with 14–18 ppm mercaptan sulfur. This treated NOS, over a month's time, developed an odor of $H_2S$ (analyzed as 3–5 ppm $H_2S$). The presence of $H_2S$ and mercaptan sulfur and possibly other impurities left in the NOS by this Cd absorbent indicates that Cd is less preferred than Cu for purifying NOS. NOS treated with $Cu(OOCCH_3)_2$ or $CdSO_4$ on silica gel contained absent 360 ppm Cu or 5–11 ppm Cd, respectively. (See Table III, Items 7, 10, 15 and 17.) A second treatment with activated alumina extrudate removed this residual metal taken up by the NOS. Two-stage treatments, first with either $Cu(OOCCH_3)_2$, $Cd(NO_3)_2$, or $CdSO_4$ on silica gel followed by activated alumina extrudate, gave acceptable values for mercaptan sulfur and metal content. (See Table III, Items 9, 11, 16 and 18, respectively.) An odor of acetic acid in NOS, treated with only $Cu(OOCCH_3)_2$ on silica gel, indicated the possible introduction of this unwanted impurity.

Copper chloride ($CuCl_2$) is used in petroleum refining "sweetening" processes and was tested also. $CuCl_2$ is of the form which allows it to be extracted by alkyl sulfides in a manner analogous to $PdCl_2$. As anticipated, experiments with $CuCl_2$ on silica gel showed substantial uptake of Cu (as indicated by an intensely green-black organic solution) by the NOS Analysis of the NOS reported 12,100 ppm Cu. (See Table III, Item 4.)

Subsequent washings with dilute HCl decreased the Cu content (refer to Table III, Items 5 and 6) but still yielded unacceptably high metal concentrations. The extracting Cu species is most likely-$CuCl_2$; at the higher chloride concentrations, some $CuCl_4^2$ or $CuCl_3(H_2O)$. exists which probably extracts as $Cl_2Cu(NOS)_2$ in the organic phase.

Silver nitrate, both in an aqueous solution and dispersed on an oxide support, was tested with NOS. Results from the experiments showed a large uptake of silver by the NOS. The photosensitivity of this silver-bearing NOS solution became apparent when, after a single day, it darkened and produced a black-brown precipitate. This photosensitivity, coupled with the ready uptake of Ag by NOS, makes Ag less desirable than Cu.

A variety of other treatments were also tried as summarized in Table III. Activated silica gel and alumina extrudate, with no metal salts, gave mediocre results (Refer to Table III, Items 2 and 3.) Caustic and HCl were tried, but results were not as good as with the above adsorbents.

$CuSO_4$ dispersed on an alumina extrudate provides complete removal of mercaptan and its by-products from NOS and also without introducing Cu into the organic in a single stage of treatment. Cu was more effective than Cd. While both lowered the mercaptan level, Cu appears to be more consistent in removing sulfur-containing by-products as measured by the total sulfur. From a toxicity viewpoint, Cu is much preferred over Cd.

Alumina is the preferred oxide support as compared to silica based upon its more efficient removal of sulfur by-products.

Obviously there are many variations on the above examples which are possible in light of the teachings supporting the present invention. It is therefore understood that within the scope of the following claims, the invention may be practiced otherwise than as specifically described herein.

What is claimed is:

1. A process for purifying alkyl sulfide containing organosulfur impurities, comprising the steps of:
   contacting the alkyl sulfide with an absorbent comprising a copper salt deposited on a porous, high area silica or alumina support in a weight ratio of metal salt to support of from about 5:1 to about 1:5;
   absorbing at least a portion of the organosulfur impurities on the absorbent to produce a purified alkyl sulfide stream having a reduced content of organosulfur impurities; and
   recovering at least a portion of the purified alkyl sulfide.

2. A process as recited in claim 1, wherein the copper salt is copper sulfate.

3. A process as recited in claim 1, wherein the support comprises alumina.

4. A process as recited in claim 1, wherein the alkyl sulfide contains from 6 to 9 carbon atoms per alkyl group.

5. A process as recited in claim 4, wherein the alkyl sulfide is n-octyl sulfide.

6. A process as recited in claim 5, wherein the organosulfur impurities include mercaptans.

7. A process as recited in claim 6, wherein the concentration of mercaptan impurities in said purified alkyl sulfide are less than about 2 ppm.

* * * * *